(12) United States Patent
Caires

(10) Patent No.: US 10,675,234 B1
(45) Date of Patent: Jun. 9, 2020

(54) SYSTEMS AND METHODS FOR TREATING AND/OR PREVENTING ACNE

(71) Applicant: N.V. Perricone LLC, San Francisco, CA (US)

(72) Inventor: Christopher Cain Caires, Larchmont, NY (US)

(73) Assignee: N.V. Perricone LLC, San Francisco, CA (US)

( * ) Notice: Subject to any disclaimer, the term of this patent is extended or adjusted under 35 U.S.C. 154(b) by 0 days.

(21) Appl. No.: 16/354,667

(22) Filed: Mar. 15, 2019

Related U.S. Application Data

(60) Provisional application No. 62/808,890, filed on Feb. 22, 2019.

(51) Int. Cl.
| | | |
|---|---|---|
| *A61K 31/60* | (2006.01) | |
| *A61K 31/194* | (2006.01) | |
| *A61K 31/198* | (2006.01) | |
| *A61K 31/245* | (2006.01) | |
| *A61K 31/7004* | (2006.01) | |
| *A61K 8/36* | (2006.01) | |
| *A61K 8/67* | (2006.01) | |
| *A61K 9/00* | (2006.01) | |

(52) U.S. Cl.
CPC .............. *A61K 8/671* (2013.01); *A61K 8/36* (2013.01); *A61K 9/0014* (2013.01); *A61K 31/194* (2013.01); *A61K 31/198* (2013.01); *A61K 31/245* (2013.01); *A61K 31/60* (2013.01); *A61K 31/7004* (2013.01)

(58) Field of Classification Search
CPC .... A61K 31/60; A61K 31/194; A61K 31/245; A61K 31/7004; A61K 8/36; A61K 8/671; A61K 9/0014
See application file for complete search history.

(56) References Cited

U.S. PATENT DOCUMENTS

| | | | | |
|---|---|---|---|---|
| 6,132,746 | A * | 10/2000 | Hasenoehrl | A61K 8/0208 424/402 |
| 2013/0289102 | A1* | 10/2013 | Singh | A61K 8/34 514/450 |
| 2018/0344624 | A1* | 12/2018 | Athwal | A61K 8/73 |

OTHER PUBLICATIONS

Bruch-Gerharz et al., Nitric oxide in human skin: current status and future prospects. J Invest Dermatol. Jan. 1998;110(1):1-7.

Smith et al., Nitric oxide precursors and congenital heart surgery: a randomized controlled trial of oral citrulline. J Thorac Cardiovasc Surg. Jul. 2006;132(1):58-65.
Wang et al., A Precision Microbiome Approach Using Sucrose for Selective Augmentation of *Staphylococcus epidermidis* Fermentation against Propionibacterium acnes. Int J Mol Sci. Nov. 9, 2016;17(11). pii: E1870.
Wang et al., *Staphylococcus epidermidis* in the human skin microbiome mediates fermentation to inhibit the growth of Propionibacterium acnes: implications of probiotics in acne vulgaris. Appl Microbiol Biotechnol. Jan. 2014;98(1):411-24. doi: 10.1007/s00253-013-5394-8. Epub Nov. 22, 2013.
International Search Report and Written Opinion for Application No. PCT/US2019/029133 dated Sep. 20, 2019.
[No Author Listed], AM to PM Gift Set. Retrieved from www.gnpd.com. Database GNPD (online) MINTEL, Nov. 8, 2018. Database accession No. 6113367.
[No Author Listed], Total Action. Retrieved from www.gnpd.com. Database GNPD (online) MINTEL, Jun. 27, 2006. Database accession No. 551050.
[No Author Listed], 4 Piece Skincare Trial & Travel Kit. Retrieved from www.gnpd.com. Database GNPD (online) MINTEL, Jun. 15, 2015. Database accession No. 3238125.
[No Author Listed], 3-Step Creates Great Skin Set. Retrieved from www.gnpd.com. Database GNPD (online) MINTEL, Oct. 23, 2017. Database accession No. 5187161.
Bundhiraja et al., Formulation and characterization of *Cucumis sativus* extract in the treatment of acne. World Journal of Pharmacy and Pharmaceutical Sciences. Nov. 16, 2014;3(12):1043-57.
Theunissen et al., Succinic acid: a promising multi-functional ingredient for cosmetic and personal-care applications. Household and Personal Care Today. Mar./Apr. 2018;13(2):42-4.

\* cited by examiner

*Primary Examiner* — Zohreh A Fay
(74) *Attorney, Agent, or Firm* — Wolf, Greenfield & Sacks, P.C.

(57) ABSTRACT

The present invention generally relates to skin care and, in particular, to systems and methods for treating and/or preventing acne. Acne is believed to be caused by a combination of factors, including *Propionibacterium acnes* bacteria, excess sebum production, and inflammation from the immune response (e.g., in response to *P. acnes*). Certain aspects of the invention are thus directed to one or more compositions that collectively target these factors, although it should be understood that a single composition may target more than one factor at a time. For instance, in one set of embodiments, a treatment may include a first composition that cleans the skin, a second composition that contains growth inhibitor of *P. acnes* (e.g., for use during the day), and a third composition that inhibits sebum production (e.g., for use during the night). One or more of these may contain other components, such as anti-inflammatory agents, moisturizers, topical anti-microbial agents (e.g., salicylic acid), or the like. Other aspects are generally directed to methods of making or use of such compositions, kits including such compositions, or the like.

17 Claims, No Drawings

SYSTEMS AND METHODS FOR TREATING AND/OR PREVENTING ACNE

RELATED APPLICATIONS

This application claims the benefit of U.S. Provisional Patent Application Ser. No. 62/808,890, filed Feb. 22, 2019, entitled "Systems and Methods for Treating and/or Preventing Acne," by C. Caires, incorporated herein by reference in its entirety.

FIELD

The present invention generally relates to skin care and, in particular, to systems and methods for treating and/or preventing acne.

BACKGROUND

Acne is a common condition affecting males and females of all ages. *Propionibacterium acnes* bacteria on the skin utilize sebum as a nutritional source. The sebum is broken down by the bacteria, subsequently releasing free fatty acids into the pilosebaceous unit causing follicular irritation, inflammation, and rupture. In addition, certain specific *P. acnes* strains demonstrated to be present in acne subjects may cause more problems than other *P. acnes* strains.

Many treatment options for acne are available, including lifestyle changes, medications, and medical procedures. However, as acne is still very widespread globally, especially among teenagers, more effective treatments are still needed.

SUMMARY

The present invention generally relates to skin care and, in particular, to systems and methods for treating and/or preventing acne. The subject matter of the present invention involves, in some cases, interrelated products, alternative solutions to a particular problem, and/or a plurality of different uses of one or more systems and/or articles.

In one aspect, the present invention is generally directed to a kit. According to a first set of embodiments, the kit comprises a first composition to the skin of a subject, wherein the cleansing composition comprises sucrose, glycerin, and salicylic acid; a second composition to the skin of the subject, wherein the second composition comprises glycerin, citrulline, succinic acid, lactic acid, and salicylic acid; and a third composition to the skin of the subject, wherein the third composition comprises glycerin, niacinamide, salicylic acid, citrulline, arginine, and retinol.

According to another set of embodiments, the kit comprises a first composition to the skin of a subject, wherein the first composition comprises at least 50 wt % of a substrate preferentially consumed by *S. epidermidis* relative to *P. acnes*; a second composition to the skin of the subject, wherein the second composition comprises a growth inhibitor of *P. acnes* and a nitric oxide donor; and a third composition to the skin of the subject, wherein the third composition comprises an anti-inflammatory agent and a sebum production inhibitor.

The kit, in yet another set of embodiments, comprises a first composition to the skin of a subject, wherein the first composition comprises at least 50 wt % glycerin; a second composition to the skin of the subject, wherein the second composition comprises (a) a nitric oxide donor, and (b) succinic acid and/or lactic acid; and a third composition to the skin of the subject, wherein the third composition comprises (a) niacinamide, (b) a nitric oxide donor, and (c) retinol.

In another aspect, the present invention is generally directed to methods of acne care, including the treatment and/or prevention of acne.

In one set of embodiments, the method comprises applying a first composition to the skin of a subject, wherein the cleansing composition comprises sucrose, glycerin, and salicylic acid; applying a second composition to the skin of the subject, wherein the second composition comprises glycerin, citrulline, succinic acid, lactic acid, and salicylic acid; and applying a third composition to the skin of the subject, wherein the third composition comprises glycerin, niacinamide, salicylic acid, citrulline, arginine, and retinol.

The method, in another set of embodiments, comprises applying a first composition to the skin of a subject, wherein the first composition comprises at least 50 wt % of a substrate preferentially consumed by *S. epidermidis* relative to *P. acnes*; applying a second composition to the skin of the subject, wherein the second composition comprises a growth inhibitor of *P. acnes* and an anti-inflammatory agent; and applying a third composition to the skin of the subject, wherein the third composition comprises an anti-inflammatory agent and a sebum production inhibitor.

In yet another set of embodiments, the method comprises applying a first composition to the skin of a subject, wherein the first composition comprises at least 50 wt % glycerin; applying a second composition to the skin of the subject, wherein the second composition comprises (a) a nitric oxide donor, and (b) succinic acid and/or lactic acid; and applying a third composition to the skin of the subject, wherein the third composition comprises (a) niacinamide, (b) a nitric oxide donor, and (c) retinol.

According to another aspect, the present invention is generally directed to a composition. In one set of embodiments, the composition comprises sucrose, glycerin, and salicylic acid. In another set of embodiments, the composition comprises at least 50 wt % of a substrate preferentially consumed by *S. epidermidis* relative to *P. acnes*. In still another set of embodiments, the composition comprises at least 50 wt % glycerin. In one set of embodiments, the composition comprises glycerin, citrulline, succinic acid, lactic acid, and salicylic acid. The composition, in another set of embodiments, comprises a growth inhibitor of *P. acnes* and a nitric oxide donor. In still another set of embodiments, the composition comprises (a) a nitric oxide donor, and (b) succinic acid and/or lactic acid. The composition, in one set of embodiments, comprises glycerin, niacinamide, salicylic acid, citrulline, arginine, and retinol. In another set of embodiments, the composition comprises an anti-inflammatory agent and a sebum production inhibitor. The composition, in accordance with still another set of embodiments, comprises (a) niacinamide, (b) a nitric oxide donor, and (c) retinol.

In another embodiment, the composition comprises each of the following ingredients at no more than +/−20% or +/−10% of the stated concentrations: water 78%, SD alcohol 40-b 3%, glycerin 3%, dicaprylyl ether 3%, niacinamide 2%, citrulline 1.5%, arginine 1.5%, methyl gluceth-20 1%, cetearyl alcohol 1%, carbomer 1%, phenoxyethanol 0.9%, citric acid 0.7%, peg-20 methyl glucose sesquistearate 0.6%, PEG-100 stearate 0.5%, salicylic acid 0.5%, glyceryl stearate 0.5%, methyl glucose sesquistearate 0.3%, xanthan gum 0.25%, sodium hydroxide 0.25%, tocopheryl acetate 0.2%, sodium benzoate 0.2%, potassium sorbate 0.2%, retinol 0.12%, Polysorbate 20 0.11%, disodium EDTA 0.1%, BHT 0.007%, tocopherol 0.001%, and *Glycine soja* (soybean) oil 0.0003%.

In still another embodiment, the composition comprises each of the following ingredients at no more than +/−20% or +/−10% of the stated concentrations: water 78%, SD alcohol 40-B 6%, glycerin 3%, $C_{12-15}$ alkyl lactate 3%, PVP 2%, dimethicone 1.8%, polysorbate 20 1%, citrulline 1%, phenoxyethanol 0.9%, squalane 0.5%, salicylic acid 0.5%, succinic acid 0.4%, polyacrylamide 0.4%, sodium benzoate 0.2%, potassium sorbate 0.2%, lactic acid 0.2%, dimethicone/vinyl dimethicone cross-polymer 0.2%, $C_{13-14}$ isoparaffin 0.2%, and laureth-7 0.06%.

In yet another embodiment, the composition comprises each of the following ingredients at no more than +/−20% or +/−10% of the stated concentrations: glycerin 81%, sodium cocoyl isethionate 7.5%, ethylhexyl palmitate 3%, silica cetly silyate 2.1%, salicylic acid 2%, sucrose 2%, phenoxyethanol 0.7%, polyacrylamide 0.4%, water 0.35%, caprylyl glycol 0.3%, $C_{13-14}$ isoparaffin 0.2%, squalane 0.1%, laureth-7 0.06%.

In addition, in still other embodiments, any one, two, three, four, or more of any of the above compositions may be present, e.g., within a kit.

Several methods are disclosed herein of administering a subject with a compound for prevention or treatment of a particular condition. It is to be understood that in each such aspect of the invention, the invention specifically includes, also, the compound for use in the treatment or prevention of that particular condition, as well as use of the compound for the manufacture of a medicament for the treatment or prevention of that particular condition.

In another aspect, the present invention encompasses methods of making one or more of the embodiments described herein, for example, one or more compositions for treating or preventing acne. In still another aspect, the present invention encompasses methods of using one or more of the embodiments described herein, for example, one or more compositions for treating or preventing acne.

Other advantages and novel features of the present invention will become apparent from the following detailed description of various non-limiting embodiments of the invention.

DETAILED DESCRIPTION

The present invention generally relates to skin care and, in particular, to systems and methods for treating and/or preventing acne. Acne is believed to be caused by a combination of factors, including *Propionibacterium acnes* bacteria, excess sebum production, and inflammation from the immune response (e.g., in response to *P. acnes*). Certain aspects of the invention are thus directed to one or more compositions that collectively target these factors, although it should be understood that a single composition may target more than one factor at a time. For instance, in one set of embodiments, a treatment may include a first composition that cleans the skin, a second composition that contains growth inhibitor of *P. acnes* (e.g., for use during the day), and a third composition that inhibits sebum production (e.g., for use during the night). One or more of these may contain other components, such as anti-inflammatory agents, moisturizers, topical anti-microbial agents (e.g., salicylic acid), or the like. Other aspects are generally directed to methods of making or use of such compositions, kits including such compositions, or the like.

Acne is believed to be the result of three factors coming together, leading to the eruption of acne lesions on the skin. In particular, *Propionibacterium acnes* bacteria grows on the skin, e.g., inside pores of the skin. Due to other physiological factors (puberty, hormones, stress, diet, etc.), the body may produce an excess amount of sebum, which can be used by *P. acnes* as a food source. The *P. acnes* bacteria, in the presence of such food, will consume the food and reproduce, and may clog the pores. This can lead to the inflammatory and/or immune response, causing swelling to the area, and the formation of acne lesions (e.g., pimples, blackheads, pustules, papules, open comedones, closed comedones, etc.), as the body fights the *P. acnes* infection. Accordingly, certain aspects of the invention are accordingly directed to systems and methods for treating some or all of these factors that cause acne by addressing *P. acnes* bacteria, oil or sebum production, and inflammation.

One example of such a treatment is now described, which uses three compositions for treating these factors. However, it should be understood that this is by way of example only, and that in other embodiments, more or fewer compositions can be used, and/or one or more of the following compositions may be used individually, i.e., without requiring the other compositions to be used. Furthermore, it should be understood that the described herein compositions need not have a one-to-one correspondence with addressing *P. acnes* bacteria, oil or sebum production, and inflammation (although they can); for example, the first composition need not only treat *P. acnes* bacteria, and may also treat oil or sebum production, and/or inflammation, etc. in various embodiments.

In one example, a subject applies a first composition to the skin in the morning to cleanse their skin, then applies a second composition during the day. In the evening, the subject may optionally apply the first composition to the skin to cleanse their skin, then applies a third composition for the night. It should be noted that this embodiment is in contrast to many other treatments in which only a single composition is ever used by a subject. In addition, it should be understood that labels such as "day" and "night" are used herein for convenience only; there is nothing about the compositions described herein that per se require the compositions to be applied at the listed times, or used throughout the day or night. Rather, these descriptions herein should be understood to be about convenience, i.e., many subjects are generally inclined to use facial products in the morning as they get ready for the day and in the evening as they prepare for sleep.

Thus, as mentioned, the first composition can be used to cleanse the skin of the subject. The first composition can be used any suitable number of times per day, e.g., once or twice (for instance, in the morning and evening, as in this example). The composition may be applied to the skin of the subject, for example, to improve facial hygiene, and/or to wash away exogenous dirt or oil, etc.

The first composition may comprise any of a wide variety of ingredients. For example, in one set of embodiments, the first composition contains ingredients such as salicylic acid, sucrose, and/or glycerin. Other examples are discussed in more detail below. Salicylic acid can act as a keratolytic and/or as acne medication. Sucrose and/or glycerin may act as fermentation substrates for *Staphylococcus epidermis*, another bacteria often found on the skin. *S. epidermis* may in some instances generate SCFA (short chain fatty acids) that selectively kill *P. acnes* bacteria using such fermentation substrates, and/or the *S. epidermis* may be able to outcompete *P. acnes* on the skin, e.g., limiting the growth of *P.*

*acnes*. Thus, for example, the first composition may contain at least 50 wt % of a substrate, such as glycerin, that is preferentially consumed by *S. epidermidis* relative to *P. acnes*. Also, glycerin may act in certain instances as a humectant and/or a skin soothing agent. This may, for example, allow for moisturizing and skin soothing benefits for reduce irritation or redness associated with acne. In addition, in some cases, relatively high amounts of glycerin may be present, e.g., at least 50 wt %, at least 60 wt %, at least 70 wt %, or at least 80 wt % glycerin. In addition, in certain embodiments, the first composition is anhydrous, e.g., as discussed below.

The second composition may act to inhibit the growth of *P. acnes*, and/or act as an anti-inflammatory agent, e.g., treating more than one of the acne-creating factors, as previously discussed. The second composition may be applied to the skin (for instance, after the first composition), and optionally allowed to remain on the skin during the day. As mentioned, it will be understood that the application of the composition for the day is about convenience (and ease of remembering) to the subject, rather than as a strict per se requirement.

The second composition may also comprise any of a wide variety of ingredients, and is discussed in more detail below. As a non-limiting example, the second composition may comprise a nitric oxide donor, and succinic acid and/or lactic acid; for example, the second composition may comprise one or more of glycerin, salicylic acid, succinic acid, lactic acid, and/or citrulline. Glycerin may act, for example, as a moisturizer and/or a fermentation substrate for *S. epidermis*, e.g., as previously discussed. Salicylic acid can act as a keratolytic and/or as acne medication. Succinic acid and lactic acid are examples of SCFAs (short chain fatty acids, such as discussed below) which may act as growth inhibitor of *P. acnes*, i.e., selectively inhibiting growth of *P. acnes* bacteria. Citrulline may act as a nitric oxide donor and/or an anti-inflammatory agent. For example, citrulline may be converted on the skin into arginine, which is a nitric oxide donor (i.e., it can react to produce nitric oxide), or an potent anti-inflammatory agent.

The third composition may act to inhibit the production of sebum, and/or act as an anti-inflammatory. Thus, the third composition may, in some cases, be used to treat more than one of the acne-creating factors. The third composition may be applied to the skin of the subject, and optionally, allowed to remain on the skin at night. In addition, in some cases, the first composition may be applied just before the third composition, e.g., to cleanse the skin. It should also be noted that, like the above compositions, the third composition need not necessarily be applied at night, but choosing to apply it at night may be more convenient for the subject.

The third composition may also comprise any of a wide variety of ingredients. For instance, the third composition may comprise niacinamide and/or retinol, and a nitric oxide donor; for example, the third composition may comprise one or more of glycerin, salicylic acid, citrulline, arginine, niacinamide, and/or retinol. Other examples of third compositions are discussed in more detail below. The glycerin may act as a moisturizer and/or a fermentation substrate for *S. epidermis*, for example, as was discussed above. Salicylic acid can act as a keratolytic and/or as acne medication. In addition, as discussed above, citrulline and/or arginine may act as a nitric oxide donor and/or an anti-inflammatory agent. Retinol and/or niacinamide can lower sebum production; as mentioned above, sebum is a food source for the *P. acnes* bacteria.

The above discussion is a non-limiting example of one embodiment of the present invention that can be used to treat acne. However, other embodiments are also possible. Accordingly, more generally, various aspects of the invention are directed to various systems and methods for skin care including systems and methods for acne treatment For instance, some aspects of the invention are generally directed to one or more compositions that are applied to the skin of a subject, e.g., a subject that has or is at risk of acne. Typically, the subject is human. The subject may be, for example, a teenager, or between 10 and 50 years old, between 10 and 40 years old, between 10 and 30 years old, or between 10 and 20 years old. The compositions described herein may be applied to the face of a subject, and/or to other areas where acne is present and/or is expected to appear, such as the neck, chest, back, etc. The amount of composition applied to the skin of the subject is not rigorously fixed, and may depend upon factors such as the type and severity of the acne, the age of the subject, etc.

In certain embodiments, compositions such as those described herein can be administered to a subject by rubbing it on the skin of the subject, e.g., in areas located at or at least within the vicinity of a desired target area, for example, at a location where acne symptoms (e.g., lesions such as papules, pustules, pimples, open comedones, closed comedones, blackheads, whiteheads, etc.) are present, or may be expected to occur. In other cases, a composition may be applied by spraying, rolling, soaking, pouring or the like onto the skin of the subject, depending on the nature of the composition. In some cases, an applicator (e.g., a gauze pad, a towel, a swab, tube, etc.), may be used to apply a composition. As other examples, a composition can be a liquid, a gel, a cream, a lotion, an ointment, a solid "stick," or the like, that can be applied to the skin, for example, by rubbing or spraying. Each of these compositions may independently be applied by the subject (e.g., self-administered), or by someone else (e.g., a parent or an aide). In addition, it should be understood that if more than one composition is used, the compositions may each independently have the same or different formulations, modes of application, etc.

As mentioned, acne is believed to be caused by a combination of bacteria, oil or sebum production, and inflammation. Examples of potentially acne-causing bacteria include *Propionibacterium acnes* (also known as *Cutibacterium acnes* or *Bacillus acnes*), *Propionibacterium avidum*, *Propionibacterium granulosum*, etc. *P. acnes* is believed to be the most common form of acne-causing bacteria, although the compositions discussed herein may be used to treat any acne-causing bacteria.

For example, in some embodiments of the invention, one or more compositions are provided that can address acne factors such as acne-causing bacteria (such as *P. acnes*), the production of sebum or oils in the skin (which acne-causing bacteria can use as a food source), and/or the inflammatory response (e.g., which may be caused when the acne-causing bacteria consume the food and reproduce, for instance, which causes clogging of pores, hair follicles, etc. within the skin). However, it should be understood that a composition need not only treat a single factor that causes acne; for example, a composition may treat two or three factors. The factor that are treated also need not be treated to the same degree.

In certain embodiments, more than one such composition may be used. For example, in various embodiments, two, three, four, or more compositions may be used, which, collectively, treat these factors of acne. It should be noted that in contrast, in many prior art systems for treating acne, only one or two factors is treated.

As an example, one or more compositions as discussed herein may be applied to the skin of a subject. For example, a first composition may be applied to the subject (e.g., as a cleanser or a rinse), optionally removed, and a second composition applied within 30 minutes, 15 minutes, or other times as described herein. After a period of time, e.g., after 3 or more hours, 6 or more hours, 9 or more hours, 12 or more hours, etc., a first composition may (again) be applied to the subject, optionally removed, and a third composition applied within 30 minutes, 15 minutes, or other times as described herein. Thus, the second and third compositions may be applied at least once per day, and the first composition may be applied once or twice per day, at least in accordance with some embodiments. As a matter of convenience, one of the second and third compositions may be applied in the morning, while the other may be applied in the evening, although other application schedules are also contemplated herein.

For example, in one aspect, a composition (e.g., a first composition) can be used as a cleanser for the skin of the subject, e.g., before applying the second and/or third compositions, or on its own. The first composition may include ingredients able to clean dirt or debris from the skin, remove excess oil, inhibit the growth of $P.$ $acnes$, deposit substrates on the skin (for example, that inhibit acne-causing bacteria), moisturize the skin, and/or remove lesions from the skin, etc. One or more ingredients able to cause any one, two, three, or more of these effects may be present in various embodiments.

For instance, in some cases, the first composition may be used to wash or rinse the skin of the subject, for example, to remove dirt or debris from the skin. The first composition may be applied to the skin, and optionally removed from the skin after a brief period of time, for example, within 30 minutes, within 15 minutes, within 10 minutes, within 5 minutes, within 3 minutes, within 2 minutes, within 1 minute, within 45 seconds, within 30 seconds, within 15 seconds, etc. The amount of time the cleanser is applied to the skin is not critical, and may vary, for example, by subject, or from day-to-day variation by the subject. For example, the subject may apply the first composition to the skin as a part of a daily routine, in which variations (e.g., in the amount applied, the time of application, etc.) from time to time are to be expected.

Afterwards, the first composition may be removed from the skin of the subject. The composition may be removed, for example, by rinsing the composition from the skin with water, wiping the composition off (for example, with a towel, with gauze pads, with cotton balls, etc.), or the like. It will be understood that the composition need not be completely removed in all cases. Removal of the first composition may assist in cleaning dirt, debris, oils, and the like from the skin, e.g., physically.

In some embodiments, the first composition may be able to inhibit the growth of $P.$ $acnes$ on the skin. For example, the first composition may contain ingredients that $P.$ $acnes$ cannot use a food source, and/or substrates that are preferentially consumed by other bacteria, such as $S.$ $epidermidis$, relative to $P.$ $acnes$ or other acne-causing bacteria. Such substrates, although they may in some cases still be consumed by $P.$ $acnes$, may nonetheless encourage the growth of other bacteria, such as $S.$ $epidermidis$, thereby leading to out-competition of $P.$ $acnes$ by the other bacteria, and thereby effectively inhibit the growth of $P.$ $acnes$ on the skin, e.g., due to the presence of the other bacteria.

In addition, bacteria such as $S.$ $epidermidis$ may in some cases produce compounds that inhibit $P.$ $acnes$ or acne-causing bacteria. For example, in some cases, $S.$ $epidermidis$ can produce fatty acids, such as short-chain fatty acids, that inhibit $P.$ $acnes$. The short-chain fatty acids may have 6, 5, 4, or fewer carbon atoms. Examples of short-chain fatty acids that can be produced by such bacteria include, but are not limited to, acetic acid, butyric acid, lactic acid, and succinic acid. In some cases, the short-chain fatty acids are able to kill $P.$ $acnes$. In contrast, many commercially available acne treatments focus on killing all bacteria on the skin, rather than selectively inhibiting $P.$ $acnes$, and are not able to encourage the growth of other bacteria that can out-compete $P.$ $acnes$ under appropriate conditions, and/or by producing species that can kill or otherwise inhibit $P.$ $acnes$.

Non-limiting examples of such substrates include sucrose and/or glycerin. Other non-limiting examples include glycerol, mannose, galactose, lactose, galactitol, saccharic acid, and/or starch. These may be present in any suitable amount or concentration. For example, the substrate may be present at at least 30 wt %, at least 40 wt %, at least 50 wt %, at least 55 wt %, at least 60 wt %, at least 65 wt %, at least 70 wt %, at least 75 wt %, at least 80 wt %, at least 85 wt %, at least 90 wt %, etc., and/or at no more than 90 wt %, no more than 85 wt %, no more than 80 wt %, no more than 75 wt %, no more than 70 wt %, no more than 65 wt %, no more than 60 wt %, no more than 55 wt %, no more than 50 wt %, no more than 40 wt %, or no more than 30 wt %. Combinations of these are also possible, e.g., a suitable substrate may be present at between 70 wt % and 90 wt %. In addition, if more than one such substrate is present, the substrates may each independently be present at the same or different concentrations.

In addition, in certain embodiments, the first composition may include one or more ingredients that can assist in moisturizing the skin. Various moisturizers or humectants may be used, and in some cases, more than one such ingredient can be used within the first composition. The ingredients may be absorbed, diffuse into, or otherwise penetrate the skin in some cases. For example, if the first composition is removed as previously discussed, some of these ingredients may be left behind to moisturize the skin afterwards.

Non-limiting examples of moisturizers and humectants include glycerin and/or squalane. Further examples include, but are not limited to, castor oil, cetyl alcohol, cetearyl alcohol, cocoa butter, isopropyl myristate, isopropyl palmitate, lanolin, liquid paraffin, polyethylene glycols, shea butter, silicone oils, stearic acid, and stearyl alcohol.

In one set of embodiments, there may be a relatively large concentration of moisturizers or humectants present within the first composition. This may be useful, for example, to ensure that a relatively large amount of moisturizer or humectant is able to moisturize the skin, e.g., during use. In contrast, many other cleansing agents are based on water, and may accordingly have relatively low concentrations of moisturizer or humectant. Certain moisturizers or humectants may have other suitable properties as well, e.g., for cleaning the skin, for inhibiting $P.$ $acnes$ such as is discussed above, and/or for other properties such as those disclosed herein.

There may be at least 30 wt %, at least 40 wt %, at least 50 wt %, at least 55 wt %, at least 60 wt %, at least 65 wt %, at least 70 wt %, at least 75 wt %, at least 80 wt %, at least 85 wt %, at least 90 wt %, etc. of one or more moisturizers and/or humectants present within the first composition in certain embodiments. In addition, in some cases, no more than 90 wt %, no more than 85 wt %, no more than 80 wt %, no more than 75 wt %, no more than 70 wt %, no more than 65 wt %, no more than 60 wt %, no more than 55 wt %, no more than 50 wt %, no more than 40 wt %, or no more than 30 wt % of the moisturizer or humectant may be present. Combinations of these are also possible, e.g., a first composition may contain between 70 wt % and 90 wt % of one or more moisturizers and/or humectants. If more than one moisturizer and/or humectant is present, they may be at the same or different concentrations.

In some embodiments, the first composition may include one or more keratolytics. Without wishing to be bound by any theory, it is believed that keratolytics generally act to remove lesions from the skin (e.g., papules, pustules, pimples, open comedones, closed comedones, blackheads, whiteheads, etc.), for example, by thinning the skin around the lesion, by unclogging the lesion, by causing the outer layer of the skin to loosen and shed, and/or by softening keratin, a major component of skin, which also may increase the skin's moisture binding capacity.

One example of a keratolytic is salicylic acid. Other non-limiting examples include alkali, urea, lactic acid, allantoin, glycolic acid, trichloroacetic acid, zinc pyrithione, sulfur, resorcinol, or the like. The keratolytic may be present in the first composition at any suitable concentration. For example, the keratolytic may be present at a concentration of at least 0.3 wt %, at least 0.5 wt %, at least 0.7 wt %, at least 1 wt %, at least 1.3 wt %, at least 1.5 wt %, at least 1.7 wt %, at least 2 wt %, at least 2.3 wt %, at least 2.5 wt %, at least 3 wt %, at least 3.5 wt %, at least 4 wt %, at least 5 wt %, etc. In addition, in some embodiments, the keratolytic may be present at a concentration of no more than 5 wt %, no more than 4 wt %, no more than 3.5 wt %, no more than 3 wt %, no more than 2.5 wt %, no more than 2.3 wt %, no more than 2 wt %, no more than 1.7 wt %, no more than 1.5 wt %, no more than 1.3 wt %, no more than 1 wt %, no more than 0.7 wt %, no more than 0.5 wt %, etc. Combinations of any of these can also be used, e.g., the keratolytic may be present between 1.7 wt % and 2.3 wt %. If more than keratolytic is present within the composition, the keratolytics may each independently have the same or different concentrations, including any of these concentrations.

In addition, in some cases, the first composition is substantially anhydrous. This may be useful, for example, to assist in moisturizing the skin, and/or preventing drying out of the skin by the first composition. For instance, there may be less than 25 wt %, less than 20 wt %, less than 15 wt %, less than 10 wt %, less than 5 wt %, less than 3 wt %, less than 2 wt %, or less than 1 wt % water present within the first composition.

As mentioned, the first composition may be used as a cleanser, for example, just before applying the second composition or the third composition, although that is not its only use. In some cases, for instance, it may be applied by itself, i.e., without necessarily applying the second composition or the third composition.

However, in one aspect, the second composition is applied after applying the first composition (and optionally, removing the first composition after a brief period of time, as noted above). The second composition may be applied for an extended period of time (e.g., several hours). As an example, the second composition can be applied in the morning, and left on the skin during the day, for example, for at least 1 hour, for at least 2 hours, at least 3 hours, at least 4 hours, at least 5 hours, at least 6 hours, at least 8 hours, at least 10 hours, at least 12 hours, etc. However, it should be understood that applying the composition during the day is essentially for the convenience of the subject; there is no per se reason that the second composition must be used only in the day. For instance, the second composition may instead be applied in the evening, and left on the skin during the night, or the second composition may be applied at other suitable or convenient times.

The second composition may include ingredients that are able to inhibit growth of acne-causing bacteria such as *P. acnes* (for example, using suitable substrates), reduce inflammation of the skin, moisturize the skin, and/or remove lesions from the skin, etc. One or more ingredients able to cause any one, two, three, or more of these can be used in different embodiments.

For example, in one set of embodiments, the second composition may contain one or more growth inhibitors of acne-causing bacteria such as *P. acnes*. Such growth inhibitors may act, for example, by killing or inhibiting growth of *P. acnes*. The growth inhibitor can include one or more fatty acids, such as short-chain fatty acids. The short-chain fatty acids may have 6, 5, 4, or fewer carbon atoms. Examples of short-chain fatty acids include succinic acid and/or lactic acid. Other non-limiting examples include acetic acid, butyric acid, etc.

The growth inhibitors may be present in the composition in any suitable amount or concentration. For example, a growth inhibitor may be present at a concentration of at least 0.1 wt %, at least 0.2 wt %, at least 0.3 wt %, at least 0.4 wt %, at least 0.5 wt %, at least 0.6 wt %, at least 0.7 wt %, at least 0.8 wt %, at least 0.9 wt %, at least 1 wt %, at least 1.2 wt %, at least 1.4 wt %, at least 1.6 wt %, at least 1.8 wt %, at least 2 wt %, at least 2.5 wt %, at least 3 wt %, at least 3.5 wt %, at least 4 wt %, at least 5 wt %, etc. In addition, in some embodiments, the growth inhibitor is present at a concentration of no more than 5 wt %, no more than 4 wt %, no more than 3.5 wt %, no more than 3 wt %, no more than 2.5 wt %, no more than 2 wt %, no more than 1.8 wt %, no more than 1.6 wt %, no more than 1.4 wt %, no more than 1.2 wt %, no more than 1 wt %, no more than 0.9 wt %, no more than 0.8 wt %, no more than 0.7 wt %, no more than 0.6 wt %, no more than 0.5 wt %, no more than 0.4 wt %, no more than 0.3 wt %, no more than 0.2 wt %, no more than 0.1 wt %, etc. Combinations of any of these are also possible in still other embodiments; for instance, a growth inhibitor may be present between 0.3 wt % and 0.5 wt %, between 0.1 wt % and 0.3 wt %, between 1.5 wt % and 2 wt %, or the like. If more than one growth inhibitor is present, the growth inhibitors may each independently be present at the same or different concentrations.

In addition, in certain cases, the second composition contains one or more ingredients that *P. acnes* cannot use a food source, and/or substrates that are preferentially consumed by other bacteria, such as *S. epidermidis*, relative to *P. acnes* or other acne-causing bacteria, e.g., in addition to or instead of a growth inhibitor such as discussed above. One non-limiting example is glycerin. Other suitable examples have been previously discussed with respect to the first concentration. One or more of these may be present within the second composition in any suitable amount or concentration, including any of those discussed above with respect to the first composition. Their concentrations within the second composition may accordingly be the same or different in the first composition.

In one set of embodiments, the second composition may contain one or more anti-inflammatory agents. For example, the second composition can include a nitric oxide (NO) donor that, when administered, can be converted into nitric oxide, which can act as an anti-inflammatory agent. For example, the NO donor may be reacted to form NO, e.g., upon exposure to air, water or moisture, bacteria, enzymes, etc., e.g., that may be present on or in the skin. Accordingly, by applying an anti-inflammatory agent such as a nitric oxide donor, the amount of inflammation within the skin, e.g., due to acne-causing bacteria, may be reduced.

Some non-limiting examples of NO donors include citrulline and/or arginine. Other examples include amyl nitrite, nitroglycerin, isosorbide dinitrate, sodium nitroprusside, S-nitrosoacetylpenacil-lamine, 3-morpholino-synoniminhydrochloride, 3-morpholino-N-athoxycarbonly-syndnonimin, isosorbide-5-monoitrite, erythrityl tetranitrate, or the like.

A nitric oxide donor, or other anti-inflammatory agent, can be present at any suitable amount or concentration, and one or more than one nitric oxide donor may be present. In some cases, a nitric oxide donor or other anti-inflammatory agent is present at a concentration of at least 0.3 wt %, at least 0.5 wt %, at least 0.7 wt %, at least 1 wt %, at least 1.3 wt %, at least 1.5 wt %, at least 1.7 wt %, at least 2 wt %, at least 2.3 wt %, at least 2.5 wt %, at least 3 wt %, at least 3.5 wt %, at least 4 wt %, at least 5 wt %, etc. In addition, in some embodiments, the nitric oxide donor or anti-inflammatory agent may be present at a concentration of no more than 5 wt %, no more than 4 wt %, no more than 3.5 wt %, no more than 3 wt %, no more than 2.5 wt %, no more than 2.3 wt %, no more than 2 wt %, no more than 1.7 wt %, no more than 1.5 wt %, no more than 1.3 wt %, no more than 1 wt %, no more than 0.7 wt %, no more than 0.5 wt %, etc. Combinations of any of these are also possible in certain cases. As a non-limiting example, a nitric oxide donor can be present between 0.7 wt % and 1.3 wt %. If more than nitric oxide donor or other anti-inflammatory agent is present within the composition, the nitric oxide donors or other agents can each independently have the same or different concentrations.

In some cases, the second composition can also include one or more ingredients that can assist in moisturizing the skin. These may include any of those previously discussed with respect to the first concentration, for example, glycerin and/or squalane, etc. One or more of these may be present within the second composition in any suitable amount or concentration, including any of those discussed above with respect to the first composition. The concentration of such ingredients within the second composition may be the same or different than the concentration in the first composition.

In addition, in accordance with certain embodiments, the second composition may include one or more keratolytics. Examples of keratolytics include salicylic acid, or others that have been discussed above. The keratolytics can be present in the second composition in any suitable amount or concentration, including any of those discussed above with respect to the first composition. The concentration of the keratolytics in the second composition thus may be the same or different than the concentration in the first composition.

In some aspects, a third composition may be applied to the skin of a subject. For example, the third composition may be applied after applying the first composition (and optionally, removing the first composition after a brief period of time, as noted above). The third composition may also be applied for extended periods of time (e.g., several hours). As an example, the third composition may be applied in the evening, and allowed to stay on the skin throughout the night. In addition, it should be understood that the subject may or may not also use the second composition as discussed above, along with the third composition. For example, in some cases, the subject may not necessarily apply the second composition, and the subject may apply the third composition in the day, or at night, or at other suitable times.

The third composition may be allowed to stay on the skin, for example, for at least 1 hour, for at least 2 hours, at least 3 hours, at least 4 hours, at least 5 hours, at least 6 hours, at least 8 hours, at least 10 hours, at least 12 hours, etc. This may occur, for example, during the night. It should be understood that applying the composition during the night is essentially for the convenience of the subject; there is no per se reason that the second composition must be used only in the night.

The third composition may include one or more ingredients that are able to inhibit sebum production, inhibit growth of acne-causing bacteria such as $P.\ acnes$ (for example, using suitable substrates), moisturize the skin, reduce inflammation of the skin, and/or remove lesions from the skin, etc. One or more than one ingredient able to cause any one, two, three, or more of these effects can be present in various embodiments.

According to certain embodiments, the third composition may contain one or more sebum production inhibitors. The sebum production inhibitors may act to reduce or prevent the production of sebum or other oils from the skin, including the production of triglycerides, wax esters, squalene, fatty acids, and the like. A variety of sebum production inhibitors may be used in various embodiments of the invention. For example, in one set of embodiments, niacinamide and/or retinol are used as sebum production inhibitors. Other non-limiting examples of sebum production inhibitors include olumacostat glasaretil, green tea extract, L-carnitine, 13-cis retinoic acid, isotretinoin, spironolactone, δ (delta)-aminolevulinic acid, cortexolone 17a-propionate, or botulinum toxin.

The sebum production inhibitors may be present in any suitable amount or concentration within the third composition. For example, a sebum production inhibitor may be present within the composition at a concentration of at least 0.1 wt %, at least 0.2 wt %, at least 0.3 wt %, at least 0.4 wt %, at least 0.5 wt %, at least 0.6 wt %, at least 0.7 wt %, at least 0.8 wt %, at least 0.9 wt %, at least 1 wt %, at least 1.2 wt %, at least 1.4 wt %, at least 1.6 wt %, at least 1.8 wt %, at least 2 wt %, at least 2.5 wt %, at least 3 wt %, at least 3.5 wt %, at least 4 wt %, at least 5 wt %, etc. In addition, in some cases, the sebum production inhibitor may be present at a concentration of no more than 5 wt %, no more than 4 wt %, no more than 3.5 wt %, no more than 3 wt %, no more than 2.5 wt %, no more than 2 wt %, no more than 1.8 wt %, no more than 1.6 wt %, no more than 1.4 wt %, no more than 1.2 wt %, no more than 1 wt %, no more than 0.9 wt %, no more than 0.8 wt %, no more than 0.7 wt %, no more than 0.6 wt %, no more than 0.5 wt %, no more than 0.4 wt %, no more than 0.3 wt %, no more than 0.2 wt %, no more than 0.1 wt %, etc. In addition, in some embodiments, combinations of any of these are also possible, e.g., a sebum production inhibitor may be present in a composition at between 0.3 wt % and 0.5 wt %, between 0.1 wt % and 0.3 wt %, between 1.5 wt % and 2 wt %, etc. If more than one sebum production inhibitor is present in a composition, the inhibitors may each independently be present at the same or different concentrations.

The third composition may also contain, in certain embodiments, one or more ingredients that $P.\ acnes$ cannot use a food source, and/or substrates that are preferentially consumed by other bacteria, such as $S.\ epidermidis$, relative to $P.\ acnes$ or other acne-causing bacteria, e.g., in addition to or instead of a growth inhibitor such as discussed above.

One non-limiting example is glycerin; other suitable examples have been previously discussed with respect to the first concentration. One or more of these may be present within the third composition in any suitable amount or concentration, including any of those discussed above with respect to the first composition. Their concentrations within the third composition may accordingly be the same or different in the first composition and/or the second composition.

In addition, in some embodiments, the third composition includes one or more ingredients that assist in moisturizing the skin. These may include any of those previously discussed with respect to the first concentration, for example, glycerin and/or squalane, etc. One or more of these may be present within the third composition in any suitable amount or concentration, including any of those discussed above with respect to the first composition. The concentration of such ingredients within the third composition can accordingly be the same or different than the concentration in the first composition and/or the second composition.

In one set of embodiments, the third composition may contain one or more anti-inflammatory agents and/or nitric oxide donors, e.g., as discussed above. Non-limiting examples include citrulline and/or arginine. These agents may be present in the third composition in any suitable amount or concentration, including any of those discussed above with respect to the first composition. In addition, their concentration within the third composition may be the same or different than the concentration in the first composition and/or the second composition.

The third composition may also include one or more keratolytics, in certain instances. Non-limiting examples of keratolytics include salicylic acid, or others that have been discussed above. The keratolytics c be present in the third composition in any suitable amount or concentration, including any of those discussed above with respect to the first composition. The concentration of the keratolytics in the third composition thus can be the same or different than the concentration in the first composition and/or the second composition.

In some aspects, formulations such as any of those described herein may each independently include a suitable carrier. Examples include, but are not limited to, water, alcohols, oils and the like. These can include sterile aqueous or nonaqueous solutions, suspensions and emulsions. Aqueous solvents may include, but are not limited to, water, alcoholic/aqueous solutions, emulsions or suspensions, including saline and buffered media. Non-limited examples of nonaqueous solvents are polypropylene glycol, polyethylene glycol, vegetable oil such as olive oil, sesame oil, coconut oil, *arachis* oil, peanut oil, mineral oil, organic esters such as ethyl oleate, or fixed oils including synthetic mono or di-glycerides. These may be chosen for their ability to dissolve or disperse ingredients (e.g., as discussed herein) at suitable concentrations. Generally, even relatively low concentrations of active ingredients may be used in accordance with certain embodiments, e.g., including any of the concentrations recited herein.

In some cases, the formulation may be one that is relatively easy to apply to the skin. Thus, for example, the formulation may take the form of a liquid (e.g., having a viscosity similar to that as water), or a viscosity significantly greater than that of water, or in some cases, the formulation may take the form of a lotion or a viscoelastic fluid. In certain embodiments, the formulation may be one that is able to form a film or layer on the skin to which it is applied. This may be useful, for example, to localize the formulation, provide some resistance to perspiration, assist in delivery of the ingredients to the skin, etc.

Many suitable formulation compositions are known to those of ordinary skill in the art, and can take the form of lotions, creams, gels or solid compositions (e.g., stick-form preparations). Typical compositions include lotions containing water and/or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These ingredients can be formulated into lotions, creams, gels, solid sticks, etc., for instance, by utilization of different proportions of the ingredients and/or by inclusion of thickening agents such as gums or other forms of hydrophillic colloids. These include carriers that are fat-soluble, i.e., those which can effectively penetrate skin layers, as well as those that are water-soluble. Those of ordinary skill in the art will be aware of systems and methods of making such formulations.

The compositions discussed herein may additionally comprise one or more adjunct ingredients, for instance, pharmaceutical drugs, skin care agents, excipients, etc. For example, a composition may include additional ingredients such as solvents, surfactants, diluents, salts, emulsifiers, buffering agents, diluents, excipients, chelating agents, fillers, drying agents, antioxidants, antimicrobials, preservatives, binding agents, bulking agents, silicas, solubilizers, or stabilizers. Preservatives and other additives may also be present such as, for example, antimicrobials, antioxidants, chelating agents and inert gases and the like. Suitable ingredients and concentrations can be determined by those of ordinary skill in the art, using no more than routine experimentation. Those of ordinary skill in the art will know of other suitable formulation ingredients, or will be able to ascertain such, using only routine experimentation.

In certain aspects, one or more of the compositions as discussed herein may be sold individually, and/or sold together within a kit. For instance, the compositions may be contained within separate containers that are packaged together within a kit, optionally with instructions for use. A kit thus may include a container, package or an assembly including one or more of the compositions as described herein, and/or other compositions. Each of the compositions of the kit may independently be provided in any suitable form, for example, as a lotion or a gel, in liquid form (e.g., in solution), or in solid form (e.g., a dried powder), or in gaseous form, etc. The compositions may be provided ready-to-use, or in some cases, the compositions may be constitutable or otherwise processable, e.g., to an active form, for example, by the addition of a suitable solvent or other species, which may or may not be provided with the kit.

A kit of the invention may, in some cases, include instructions in any form that are provided in connection with the compositions of the invention in such a manner that would be recognized such that the instructions are to be associated with the compositions contained therein. For instance, the instructions may include instructions for the use, modification, mixing, diluting, preserving, administering, assembly, storage, packaging, and/or preparation of compositions associated with the kit. In some cases, the instructions may also include instructions for the delivery and/or administration of the compositions, for example, for a particular use, e.g., to the skin of a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

U.S. Provisional Patent Application Ser. No. 62/808,890, filed Feb. 22, 2019, entitled "Polymer Solid Electrolytes," is incorporated herein by reference in its entirety. The following examples are intended to illustrate certain embodiments of the present invention, but do not exemplify the full scope of the invention.

Example 1

One method for treating acne is to remove sebum, which reduces the number of P. acnes organisms capable of surviving on the skin surface, thus possibly reducing the severity of acne. In addition to sebum removal, cleansers can be augmented with the use of keratolytic agents, such as salicylic acid. Certain embodiments described herein are generally directed to systems and methods that target the three causes of acne (bacteria, inflammation, and excess oil). For example, in this example, three compositions are described that can be used to treat these causes.

The first composition is a cleanser, which is low foaming and anhydrous. It is very thick (e.g., having a relatively high viscosity), so one should be patient when dispensing it. It should be worked into a light lather using hands and used to wash the face of the subject. The subject may feel a burst of warmth. The subject may be left on for about 30 seconds or so, e.g., until the warmth subsides. This cleanser is different than almost every other cleanser. Rather than only washing away oil and bacteria, it can also remove excess oil while simultaneously depositing oil and hydrators that acne bacteria cannot feed on. The subject thus can experience clean, hydrated skin that does not cause breakouts. The subject's face may thus not be dried out.

The first composition may cleanse the skin, reduce excess oil, unclog pores, removes dead skin cells, and/or eliminates debris, e.g., without irritating the skin. This may be particularly beneficial, for example, with subjects with sensitive, acne-prone skin. The sucrose may support a healthy surface skin microbiome, yet rinse off quickly and easily. The squalane may hydrate the skin without making skin look or feel greasy.

In the morning, the subject may apply the second composition, which is a prebiotic lotion. This may be applied after using the cleanser. Nearly all acne treatment brands rely on some type of antibiotic like benzoyl peroxide or sulfur that just kills facial bacteria. This may have unwanted side effects, such as of irritating the skin while causing a vicious cycle of killing bad acne, causing bacteria that just grows right back. In contrast, the second composition contains ingredients that work with the skin's natural microbiome, e.g., by selectively feeding the "good bacteria" (S. epidermis) and killing the "bad bacteria" (e.g., P. acnes). This may keep the "bad bacteria" at bay, eliminating a major cause of acne.

The second composition can be used in the day or morning, e.g., after cleansing. The lightweight lotion may glide onto skin to kill acne-causing bacteria, while nourishing the skin with essential hydration. Lactic acid and succinic acid may be used to support a healthy surface skin microbiome for a clearer, more radiant complexion. Citrulline and squalane may fight irritation, nourish, hydrate, soothe, and/or visibly reduces redness.

In the evening, the subject may use the cleanser again, following up with a third composition, which is a night-time oil control lotion. This lotion works to suppress excess oil production and tamp down inflammation. It may also reduce acne blemishes and scarring over time, and/or reduce wrinkles.

The third composition can be used in the night, e.g., after cleansing. The lightweight yet nourishing formula can be absorbed into the skin and help to control excess oil. The combination of retinol, citrulline, and niacinamide may help to accelerate surface skin exfoliation and renewal, visibly calm skin, reduce redness, and/or gently and visibly erase imperfections overnight.

Example 2

This example illustrates various compositions usable to treat acne, in accordance with another embodiment of the invention. These compositions can be used, e.g., as described above. In some cases, the compositions may be present at +/−20% or +/−10% of the stated concentrations. For example, there may be variations in the product created by variations in the fabrication process, or from different material sources.

The first composition is a cleanser. The cleanser is anhydrous and contains ingredients 2% sucrose, 81.3% glycerin, 0.1% squalane, and 2% salicylic acid. The exact composition used in this example is shown in Table 1:

TABLE 1

| Ingredient | Weight Percent |
|---|---|
| Glycerin | 81.3% |
| Sodium cocoyl isethionate | 7.5% |
| Ethylhexyl palmitate | 3% |
| Silica cetly silyate | 2.1% |
| Salicylic acid | 2% |
| Sucrose | 2% |
| Phenoxyethanol | 0.7% |
| Polyacrylamide | 0.4% |
| Water | 0.345% |
| Caprylyl glycol | 0.3% |
| $C_{13-14}$ isoparaffin | 0.2% |
| Squalane | 0.1% |
| Laureth-7 | 0.055% |

The second composition is a lotion. It includes 3% glycerin, 1% citrulline, 0.4% succinic acid, 0.2% lactic acid, and 0.5% salicylic acid. The exact composition used in this example is shown in Table 2.

TABLE 2

| Ingredient | Weight Percent |
|---|---|
| Water | 78.445% |
| SD Alcohol 40-B | 6% |
| Glycerin | 3% |
| $C_{12-15}$ alkyl Lactate | 3% |
| PVP | 2% |
| Dimethicone | 1.8% |
| Polysorbate 20 | 1% |
| Citrulline | 1% |
| Phenoxyethanol | 0.9% |
| Squalane | 0.5% |
| Salicylic acid | 0.5% |
| Succinic acid | 0.4% |
| Polyacrylamide | 0.4% |
| Sodium benzoate | 0.2% |

TABLE 2-continued

| Ingredient | Weight Percent |
| --- | --- |
| Potassium sorbate | 0.2% |
| Lactic acid | 0.2% |
| Dimethicone/vinyl dimethicone cross-polymer | 0.2% |
| $C_{13-14}$ isoparaffin | 0.2% |
| Laureth-7 | 0.055% |

The third composition is also a lotion. It includes 3% glycerin, 2% niacinamide, 0.5% salicylic acid, 1.5% citrulline, 1.5% arginine, 0.115% retinol. The exact composition used in this example is shown in Table 3.

TABLE 3

| Ingredient | Weight Percent |
| --- | --- |
| Water | 77.57% |
| SD Alcohol 40-B | 3% |
| Glycerin | 3% |
| Dicaprylyl ether | 2.99883% |
| Niacinamide | 2% |
| Citrulline | 1.5% |
| Arginine | 1.5% |
| Methyl Gluceth-20 | 1% |
| Cetearyl alcohol | 1% |
| Carbomer | 1% |
| Phenoxyethanol | 0.9% |
| Citric acid | 0.7% |
| PEG-20 methyl glucose sesquistearate | 0.59985% |
| PEG-100 Stearate | 0.5% |
| Salicylic acid | 0.5% |
| Glyceryl stearate | 0.5% |
| Methyl glucose sesquistearate | 0.3% |
| Xanthan gum | 0.25% |
| Sodium hydroxide | 0.25% |
| Tocopheryl acetate | 0.2% |
| Sodium benzoate | 0.2% |
| Potassium sorbate | 0.2% |
| Retinol | 0.115% |
| Polysorbate 20 | 0.1081% |
| Disodium EDTA | 0.1% |
| BHT | 0.0069% |
| Tocopherol | 0.00105% |
| Glycine soja (soybean) oil | 0.00027% |

Example 3

In this example, the compositions of Example 2 and control formulations were applied to 64 acne subjects over a period of 8 weeks. The subjects were 15-30 year old male and female subjects with mild acne. For each subject, the cleanser was applied in the morning followed by rinsing and application of the second composition (called the "day" composition), then the cleanser was applied in the evening followed by rinsing and application of the third composition (called the "night" composition). The subjects were evaluated for acne, lesion counts (papules, pustules, open comedones, closed comedones), and tolerability. In addition, the subjects underwent facial microbiome swabbing.

The goals of these experiments included evaluating the effect of this approach on bacterial management of the face, demonstrating inflammatory and non-inflammatory lesion count reduction following 8 weeks of use, and demonstrating tolerability of this approach.

Some conclusions of these experiments were as follows. Subjects rated their skin as having significantly less acne at both 4 and 8 weeks. The subjects had significantly less whiteheads (closed comedones) and red swollen bumps (papules) at both 4 and 8 weeks. In addition, the subjects had significantly less whiteheads (closed comedones) and red swollen bumps (papules) at 8 weeks compared to a group using a placebo formula. The subjects had significantly less acne and improved appearance at both 4 and 8 weeks, and also had significantly less acne and improved appearance at 8 weeks compared to a group using a placebo formula.

The formulations did not cause an increase in burning, redness, drying, or scaling over the course of 8 weeks, and the formulations did not cause burning, redness, drying, scaling, and stinging that was any different than the placebo. The formulations were found to be non-irritating.

The subjects reported that the formulations did not cause any increase in redness, scaling, or stinging after 4 weeks of use, and that the formulations did not cause any increase in burning, redness, scaling, or stinging after 8 weeks of use.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A kit, comprising:
a first container comprising a first, morning composition for application to the skin of a subject, wherein the first composition comprises each of the following ingredients at no more than +/−20% of the stated concentrations, by weight:
Glycerin 81%
Salicylic acid 2%
Sucrose 2%;
a second container comprising a second, day composition for application to the skin of the subject, wherein the second composition comprises each of the following ingredients at no more than +/−20% of the stated concentrations, by weight:
Water 78%
Glycerin 3%
Citrulline 1%
Salicylic acid 0.5%
Succinic acid 0.4%
Lactic acid 0.2%; and
a third container comprising a third, night composition for application to the skin of the subject, wherein the third composition comprises each of the following ingredients at no more than +/−20% of the stated concentrations, by weight:
Water 78%
Glycerin 3%
Niacinamide 2%
Citrulline 1.5%
Arginine 1.5%
Salicylic acid 0.5%
Retinol 0.12%.

2. The kit of claim 1, wherein the first composition comprises less than 5 wt % water.

3. The kit of claim 1, wherein the first composition comprises at least 50 wt % glycerin.

4. The kit of claim 1, wherein the first composition is a lotion.

5. The kit of claim 1, wherein the second composition is a lotion.

6. The kit of claim 1, wherein the third composition is a lotion.

7. The kit of claim 1, wherein the first composition, the second composition, and the third composition are each individually contained within the kit.

8. The kit of claim 1, wherein the first composition consists essentially of glycerin, sodium cocoyl isethionate, ethylhexyl palmitate, silica cetly silyate, salicylic acid, sucrose, phenoxyethanol, polyacrylamide, water, caprylyl glycol, $C_{13-14}$ isoparaffin, squalane, and laureth-7.

9. The kit of claim 1, wherein the second composition consists essentially of water, SD alcohol 40-B, glycerin, $C_{12-15}$ alkyl lactate, PVP, dimethicone, Polysorbate 20, citrulline, phenoxyethanol, squalane, salicylic acid, succinic acid, polyacrylamide, sodium benzoate, potassium sorbate, lactic acid, dimethicone/vinyl dimethicone cross-polymer, $C_{13-14}$ isoparaffin, and laureth-7.

10. The kit of claim 1, wherein the third composition consists essentially of water, SD alcohol 40-B, glycerin, dicaprylyl ether, niacinamide, citrulline, arginine, methyl gluceth-20, cetearyl alcohol, carbomer, phenoxyethanol, citric acid, PEG-20 methyl glucose sesquistearate, PEG-100 stearate, salicylic acid, glyceryl stearate, methyl glucose sesquistearate, xanthan gum, sodium hydroxide, tocopheryl acetate, sodium benzoate, potassium sorbate, retinol, Polysorbate 20, disodium EDTA, BHT, tocopherol, and *Glycine soja* (soybean) oil.

11. The kit of claim 1, wherein the first composition comprises each of the following ingredients at no more than +/−20% of the stated concentrations, by weight:
Glycerin 81%
Sodium cocoyl isethionate 7.5%
Ethylhexyl palmitate 3%
Silica cetly silyate 2.1%
Salicylic acid 2%
Sucrose 2%
Phenoxyethanol 0.7%
Polyacrylamide 0.4%
Water 0.35%
Caprylyl glycol 0.3%
$C_{13-14}$ isoparaffin 0.2%
Squalane 0.1%
Laureth-7 0.06%.

12. The kit of claim 1, wherein the second composition comprises each of the following ingredients at no more than +/−20% of the stated concentrations, by weight:
Water 78%
SD Alcohol 40-B 6%
Glycerin 3%
$C_{12-15}$ alkyl Lactate 3%
PVP (polyvinylpyrrolidone) 2%
Dimethicone 1.8%
Polysorbate 20 1%
Citrulline 1%
Phenoxyethanol 0.9%
Squalane 0.5%
Salicylic acid 0.5%
Succinic acid 0.4%
Polyacrylamide 0.4%
Sodium benzoate 0.2%
Potassium Sorbate 0.2%
Lactic acid 0.2%
Dimethicone/vinyl dimethicone cross-polymer 0.2%
$C_{13-14}$ isoparaffin 0.2%
Laureth-7 0.06%.

13. The kit of claim 1, wherein the third composition comprises each of the following ingredients at no more than +/−20% of the stated concentrations, by weight:
Water 78%
SD Alcohol 40-B 3%
Glycerin 3%
Dicaprylyl ether 3%
Niacinamide 2%
Citrulline 1.5%
Arginine 1.5%
Methyl Gluceth-20 1%
Cetearyl alcohol 1%
Carbomer 1%
Phenoxyethanol 0.9%
Citric acid 0.7%
PEG-20 methyl glucose sesquistearate 0.6%
PEG-100 Stearate 0.5%
Salicylic acid 0.5%
Glyceryl stearate 0.5%
Methyl glucose sesquistearate 0.3%
Xanthan gum 0.25%
Sodium hydroxide 0.25%
Tocopheryl acetate 0.2%
Sodium benzoate 0.2%
Potassium sorbate 0.2%
Retinol 0.12%
Polysorbate 20 0.11%
Disodium EDTA 0.1%
BHT 0.007%
Tocopherol 0.001%
*Glycine soja* (soybean) oil 0.0003%.

14. A method of acne care, the method comprising:
applying a first morning composition to the skin of a subject, wherein the cleansing composition comprises each of the following ingredients at no more than +/−20% of the stated concentrations, by weight:
Glycerin 81%
Salicylic acid 2%
Sucrose 2%;
applying a second day composition to the skin of the subject, wherein the second composition comprises each of the following ingredients at no more than +/−20% of the stated concentrations, by weight:
Water 78%
Glycerin 3%
Citrulline 1%
Salicylic acid 0.5%
Succinic acid 0.4%
Lactic acid 0.2%; and
applying a third night composition to the skin of the subject, wherein the third composition comprises each of the following ingredients at no more than +/−20% of the stated concentrations, by weight:
Water 78%
Glycerin 3%
Niacinamide 2%
Citrulline 1.5%
Arginine 1.5%
Salicylic acid 0.5%
Retinol 0.12%.

15. The method of claim 14, wherein applying the second composition and applying the third composition are separated by at least 6 hours.

16. The method of claim 14, comprising applying each of the first, second, and third compositions at least once per day.

17. The method of claim 14, comprising applying the first composition within 30 minutes before applying the second composition or the third composition.

* * * * *